United States Patent
Ohno et al.

(10) Patent No.: US 8,497,391 B2
(45) Date of Patent: Jul. 30, 2013

(54) INSULATING FILM MATERIAL, METHOD OF FILM FORMATION USING INSULATING FILM MATERIAL, AND INSULATING FILM

(75) Inventors: Takahisa Ohno, Tsukuba (JP); Nobuo Tajima, Tsukuba (JP); Satoshi Hasaka, Oyama (JP); Minoru Inoue, Tokyo (JP); Kaoru Sakoda, Yokohama (JP); Yoshiaki Inaishi, Kawasaki (JP); Manabu Shinriki, Kawaguchi (JP); Kazuhiro Miyazawa, Yokohama (JP)

(73) Assignees: National Institute for Materials Science, Tsukuba-shi, Ibaraki (JP); Taiyo Nippon Sanso Corporation, Tokyo (JP)

( * ) Notice: Subject to any disclaimer, the term of this patent is extended or adjusted under 35 U.S.C. 154(b) by 277 days.

(21) Appl. No.: 12/864,127

(22) PCT Filed: Jan. 20, 2009

(86) PCT No.: PCT/JP2009/050782
§ 371 (c)(1),
(2), (4) Date: Jul. 22, 2010

(87) PCT Pub. No.: WO2009/093581
PCT Pub. Date: Jul. 30, 2009

(65) Prior Publication Data
US 2011/0130584 A1      Jun. 2, 2011

(30) Foreign Application Priority Data
Jan. 23, 2008   (JP) ................ P2008-013105

(51) Int. Cl.
*C23C 16/00* (2006.01)
*C07F 7/08* (2006.01)
*H01L 21/31* (2006.01)

(52) U.S. Cl.
USPC ........................................... 556/406

(58) Field of Classification Search
None
See application file for complete search history.

(56) References Cited

U.S. PATENT DOCUMENTS

| | | | |
|---|---|---|---|
| 7,189,664 B2 | 3/2007 | Loboda | |
| 2004/0166692 A1 | 8/2004 | Loboda | |
| 2006/0079099 A1 | 4/2006 | Nguyen | |
| 2006/0148252 A1 | 7/2006 | Loboda | |

FOREIGN PATENT DOCUMENTS

| | | |
|---|---|---|
| JP | 2005-045058 | 2/2005 |
| JP | 2006-519496 | 8/2006 |

OTHER PUBLICATIONS

Matsumoto et al Macromolecules, 2002, 35, 555-565.*
Block et al. Journal of the American Chemical Society, 1978, 100(5), 1630-1632.*
International Search Report for PCT/JP2009/050782, mailed Feb. 17, 2009.
Loke et al, "Kinetics of Copper Drift in Low-k Polymer Interlevel Dielectrics", IEEE Transactions on Electron Devices, vol. 46, No. 11, Nov. 1999.

* cited by examiner

*Primary Examiner* — Yevegeny Valenrod
(74) *Attorney, Agent, or Firm* — Nixon & Vanderhye P.C.

(57) ABSTRACT

An insulating film material for plasma CVD represented by a chemical formula (1) shown below, a method of film formation using the insulating film material, and an insulating film. According to the present invention, an insulating film having a low dielectric constant and a superior copper diffusion barrier property suitable for an interlayer insulating film or the like of a semiconductor device can be obtained. In the chemical formula (1), n represents an integer of 3 to 6, and each of $R^1$ and $R^2$ independently represents one of $C_2H$, $C_2H_3$, $C_3H_3$, $C_3H_5$, $C_3H_7$, $C_4H_5$, $C_4H_7$, $C_4H_9$, $C_5H_7$, $C_5H_9$ and $C_5H_{11}$.

[Chemical formula 1]

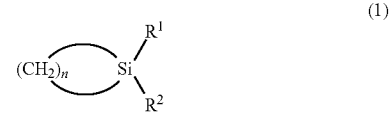

(1)

4 Claims, 4 Drawing Sheets

INSULATING FILM MATERIAL, METHOD OF FILM FORMATION USING INSULATING FILM MATERIAL, AND INSULATING FILM

This application is the U.S. national phase of International Application No. PCT/JP2009/050782, filed 20 Jan. 2009, which designated the U.S. and claims priority to Japanese application no. 2008-013105, filed 23 Jan. 2008, the entire contents of each of which are hereby incorporated by reference.

TECHNICAL FIELD

The present invention relates to an insulating film material used in the formation of an insulating film that is useful as an interlayer insulating film or the like within a semiconductor device, and also relates to a method of film formation that uses the insulating film material, and an insulating film. According to the present invention, an insulating film having a low dielectric constant and a superior copper diffusion barrier property can be obtained.

Priority is claimed on Japanese Patent Application No. 2008-013105, filed Jan. 23, 2008, the content of which is incorporated herein by reference.

BACKGROUND ART

As the levels of integration within semiconductor devices increase, the wiring layers continue to become increasingly miniaturized. However, in these very fine wiring layers, the effects of signal delays within the wiring layer tend to increase, impeding increases in the signal transmission speed.

These signal delays are proportional to the resistance of the wiring layer and the capacity between wiring layers, and therefore in order to achieve higher transmission speeds, the resistance of the wiring layers and the capacity between wiring layers must be reduced.

Accordingly, in recent years there has been a change in the materials used in forming the wiring layers, from the more conventional aluminum to low resistivity copper, whereas interlayer insulating films having a low dielectric constant are now being used to reduce the capacity between wiring layers.

For example, an $SiO_2$ film has a dielectric constant of 4.1 and an SiOF film has a dielectric constant of 3.7, but recently, SiOCH films and organic films having even lower dielectric constants are starting to be used.

In this manner, the dielectric constant of interlayer insulating films continues to decrease gradually, and much research is being conducted into the development of low dielectric constant interlayer insulating films having a dielectric constant of 2.4 or lower for next generation applications. Interlayer insulating films for which the dielectric constant is less than 2.0 have also been reported recently.

Further, in multilayer wiring structures that use copper for the wiring layers, an insulating film having a copper diffusion barrier property is inserted at each interface between a copper wiring layer and an insulating film in order to prevent diffusion of the copper into the insulating film.

An insulating film composed of silicon nitride or SiCN or the like, which exhibit superior copper diffusion barrier properties, is typically used for this copper diffusion barrier insulating film, but such films have a high dielectric constant of 4 to 7, which increases the effective dielectric constant of the overall insulating film that constitutes the multilayer wiring structure.

For example, in a multilayer wiring structure in which an interlayer insulating film having a dielectric constant of approximately 2.5 is laminated to a copper diffusion barrier insulating film having a dielectric constant of approximately 4, the effective dielectric constant is approximately 3.

In other words, in order to lower the effective dielectric constant, a reduction in the dielectric constant of the copper diffusion barrier insulating film is required, and considerable research and development aimed at achieving that goal is currently in progress.

Previously, a copper diffusion barrier insulating film which uses an organosilane material having π-electron bonds and is composed mainly of silicon and carbon has been reported (see Patent Document 1).

[Patent Document 1]
Japanese Unexamined Patent Application, First Publication No. 2005-45058

DISCLOSURE OF INVENTION

However, the dielectric constant of the copper diffusion barrier insulating film disclosed within the prior invention mentioned above is a relatively high value of 3.9, and moreover, the insulating film cannot be claimed to provide a significantly superior copper diffusion barrier property to that provided by conventional copper diffusion barrier insulating films composed of SiCN.

Accordingly, an object of the present invention is to provide an insulating film that has a favorable copper diffusion barrier property and also has an extremely low dielectric constant.

In order to achieve the above object, the present invention employs the constitutions described below.

[1] An insulating film material for plasma CVD, represented by chemical formula (1) shown below.

[Chemical Formula 1]

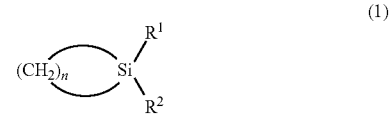

(1)

In chemical formula (1), n represents an integer of 3 to 6, and each of $R^1$ and $R^2$ independently represents one of $C_2H$, $C_2H_3$, $C_3H_3$, $C_3H_5$, $C_3H_7$, $C_4H_5$, $C_4H_7$, $C_4H_9$, $C_5H_7$, $C_5H_9$ and $C_5H_{11}$.

[2] A method of film formation, comprising using the insulating film material according to [1] above to form an insulating film by a plasma CVD method.

[3] The method of film formation according to [2] above, wherein a carrier gas is not supplied during film formation.

[4] An insulating film, obtained by the method of film formation according to [2] or [3] above.

According to the present invention, an insulating film formed by a plasma CVD method using a silicon compound represented by the above chemical formula (1) as the insulating film material has a low dielectric constant and exhibits a superior copper diffusion barrier property.

DESCRIPTION OF THE REFERENCE SYMBOLS

Figure 1:
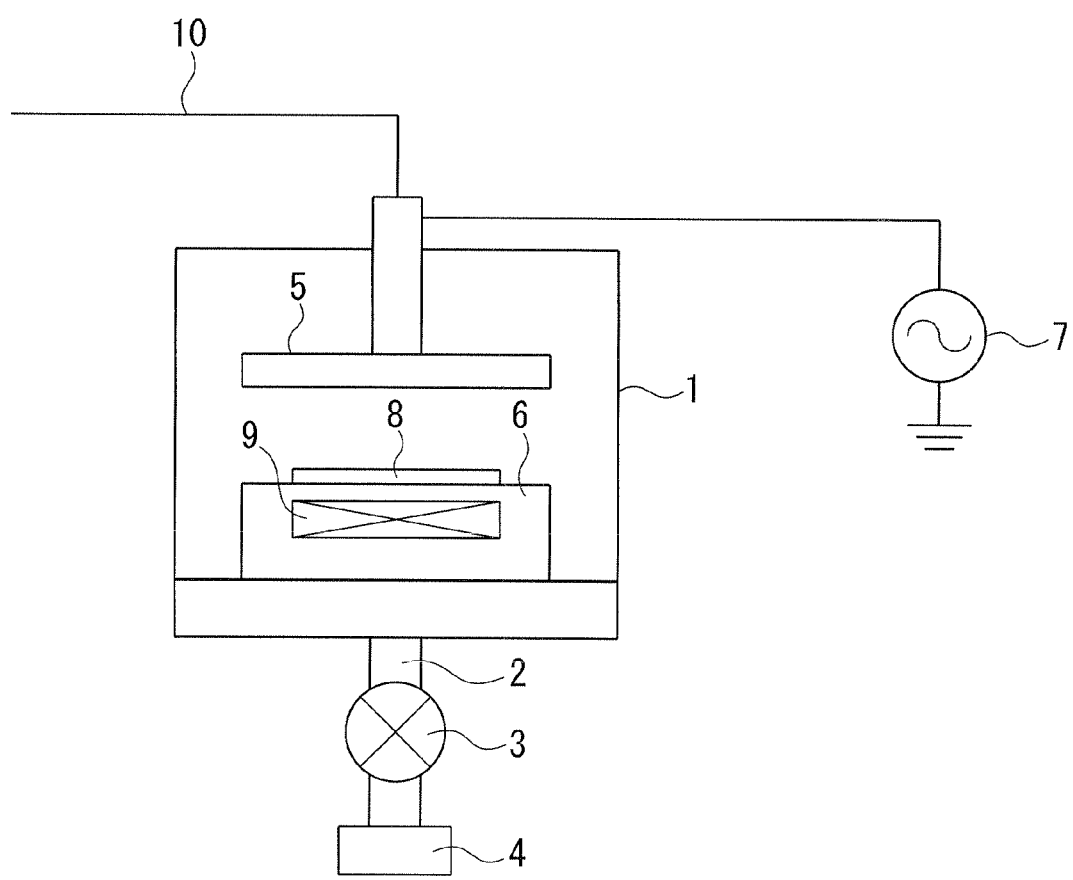
FIG. 1 is a schematic structural diagram illustrating one example of a film formation apparatus used in the method of film formation according to the present invention.

1: Chamber
2: Exhaust pipe
3: On-off valve
4: Exhaust pump
5: Upper electrode
6: Lower electrode
7: High-frequency power source
8: Substrate
9: Heater
10: Gas supply pipe Best Mode For Carrying Out The Invention A more detailed description of the present invention is presented below.

An insulating film material for plasma CVD according to the present invention is a silicon compound represented by the above chemical formula (1). All of the compounds of this formula are known compounds, and can be obtained using conventional synthesis methods. The use of compounds represented by this chemical formula (1) as copper diffusion barrier insulating film materials is currently unknown.

In this silicon compound, 3 to 6 —$CH_2$— groups are bonded together to form a 3-membered to 6-membered cyclic structure, wherein the carbon atoms at the end of the cyclic chain are bonded to a silicon atom. The resulting cyclic structure includes no double bonds.

The substituents $R^1$ and $R^2$ within a single molecule of the compound may be either the same substituent or different substituents.

In the silicon compound represented by the above chemical formula (1), if the number of carbon atoms within the substituent $R^1$ is termed X and the number of carbon atoms within the substituent $R^2$ is termed Y, then those compounds that satisfy the relationship: n=X+Y (wherein n is the number of $CH_2$ bonds within the chemical formula (1)) are preferred in terms of the lowness of the dielectric constant of the formed insulating film, the existence of a favorable copper diffusion barrier property, and the mechanical strength of the insulating film. Further, $R^1$ and $R^2$ are preferably the same substituent.

Specific examples of preferred compounds represented by chemical formula (1) include 1,1-divinyl-1-silacyclopentane and 1,1-diallyl-1-silacyclopentane.

Examples of other silicon compounds which may be used include 1,1-diethynyl-1-silacyclobutane, 1,1-divinyl-1-silacyclobutane, 1,1-di-1-propynyl-1-silacyclobutane, 1,1-di-2-propynyl-1-silacyclobutane, 1,1-dipropenyl-1-silacyclobutane, 1,1-diallyl-1-silacyclobutane, 1,1-dipropyl-1-silacyclobutane, 1,1-diisopropyl-1-silacyclobutane, 1,1-di-1-butynyl-1-silacyclobutane, 1,1-di-2-butynyl-1-silacyclobutane, 1,1-di-3-butynyl-1-silacyclobutane, 1,1-di-1-butenyl-1-silacyclobutane, 1,1-di-2-butenyl-1-silacyclobutane, 1,1-di-3-butenyl-1-silacyclobutane, 1,1-dicyclobutyl-1-silacyclobutane, 1,1-dibutyl-1-silacyclobutane, 1,1-di-s-butyl-1-silacyclobutane, 1,1-di-t-butyl-1-silacyclobutane, 1,1-di-1-pentynyl-1-silacyclobutane, 1,1-di-2-pentynyl-1-silacyclobutane, 1,1-di-3-pentynyl-1-silacyclobutane, 1,1-di-1-pentenyl-1-silacyclobutane, 1,1-di-2-pentenyl-1-silacyclobutane, 1,1-di-3-pentenyl-1-silacyclobutane, 1,1-di-4-pentenyl-1-silacyclobutane, 1,1-dicyclopentyl-1-silacyclobutane, 1,1-dipentyl-1-silacyclobutane, 1,1-di-t-pentyl-1-silacyclobutane, 1,1-diethynyl-1-silacyclopentane, 1,1-divinyl-1-silacyclopentane, 1,1-di-1-propynyl-1-silacyclopentane, 1,1-di-2-propynyl-1-silacyclopentane, 1,1-dipropenyl-1-silacyclopentane, 1,1-diallyl-1-silacyclopentane, 1,1-dipropyl-1-silacyclopentane, 1,1-diisopropyl-1-silacyclopentane, 1,1-di-1-butynyl-1-silacyclopentane, 1,1-di-2-butynyl-1-silacyclopentane, 1,1-di-3-butynyl-1-silacyclopentane, 1,1-di-1-butenyl-1-silacyclopentane, 1,1-di-2-butenyl-1-silacyclopentane, 1,1-di-3-butenyl-1-silacyclopentane, 1,1-dicyclobutyl-1-silacyclopentane, 1,1-dibutyl-1-silacyclopentane, 1,1-di-s-butyl-1-silacyclopentane, 1,1-di-t-butyl-1-silacyclopentane, 1,1-di-1-pentynyl-1-silacyclopentane, 1,1-di-2-pentynyl-1-silacyclopentane, 1,1-di-3-pentynyl-1-silacyclopentane, 1,1-di-1-pentenyl-1-silacyclopentane, 1,1-di-2-pentenyl-1-silacyclopentane, 1,1-di-3-pentenyl-1-silacyclopentane, 1,1-di-4-pentenyl-1-silacyclopentane, 1,1-dicyclopentyl-1-silacyclopentane, 1,1-dipentyl-1-silacyclopentane, 1,1-di-t-pentyl-1-silacyclopentane, 1,1-diethynyl-1-silacyclohexane, 1,1-divinyl-1-silacyclohexane, 1,1-di-1-propynyl-1-silacyclohexane, 1,1-di-2-propynyl-1-silacyclohexane, 1,1-dipropenyl-1-silacyclohexane, 1,1-diallyl-1-silacyclohexane, 1,1-dipropyl-1-silacyclohexane, 1,1-diisopropyl-1-silacyclohexane, 1,1-di-1-butynyl-1-silacyclohexane, 1,1-di-2-butynyl-1-silacyclohexane, 1,1-di-3-butynyl-1-silacyclohexane, 1,1-di-1-butenyl-1-silacyclohexane, 1,1-di-2-butenyl-1-silacyclohexane, 1,1-di-3-butenyl-1-silacyclohexane, 1,1-dicyclobutyl-1-silacyclohexane, 1,1-dibutyl-1-silacyclohexane, 1,1-di-s-butyl-1-silacyclohexane, 1,1-di-t-butyl-1-silacyclohexane, 1,1-di-1-pentynyl-1-silacyclohexane, 1,1-di-2-pentynyl-1-silacyclohexane, 1,1-di-3-pentynyl-1-silacyclohexane, 1,1-di-1-pentenyl-1-silacyclohexane, 1,1-di-2-pentenyl-1-silacyclohexane, 1,1-di-3-pentenyl-1-silacyclohexane, 1,1-di-4-pentenyl-1-silacyclohexane, 1,1-dicyclopentyl-1-silacyclohexane, 1,1-dipentyl-1-silacyclohexane, 1,1-di-t-pentyl-1-silacyclohexane, 1,1-diethynyl-1-silacycloheptane, 1,1-divinyl-1-silacycloheptane, 1,1-di-1-propynyl-1-silacycloheptane, 1,1-di-2-propynyl-1-silacycloheptane, 1,1-dipropenyl-1-silacycloheptane, 1,1-diallyl-1-silacycloheptane, 1,1-dipropyl-1-silacycloheptane, 1,1-diisopropyl-1-silacycloheptane, 1,1-di-1-butynyl-1-silacycloheptane, 1,1-di-2-butynyl-1-silacycloheptane, 1,1-di-3-butynyl-1-silacycloheptane, 1,1-di-1-butenyl-1-silacycloheptane, 1,1-di-2-butenyl-1-silacycloheptane, 1,1-di-3-butenyl-1-silacycloheptane, 1,1-dicyclobutyl-1-silacycloheptane, 1,1-dibutyl-1-silacycloheptane, 1,1-di-s-butyl-1-silacycloheptane, 1,1-di-t-butyl-1-silacycloheptane, 1,1-di-1-pentynyl-1-silacycloheptane, 1,1-di-2-pentynyl-1-silacycloheptane, 1,1-di-3-pentynyl-1-silacycloheptane, 1,1-di-1-pentenyl-1-silacycloheptane, 1,1-di-2-pentenyl-1-silacycloheptane, 1,1-di-3-pentenyl-1-silacycloheptane, 1,1-di-4-pentenyl-1-silacycloheptane, 1,1-dicyclopentyl-1-silacycloheptane, 1,1-dipentyl-1-silacycloheptane and 1,1-di-t-pentyl-1-silacycloheptane.

Next is a description of a method of film formation according to the present invention.

The method of film formation according to the present invention is basically a method of forming a film by a plasma CVD method using the aforementioned insulating film material represented by chemical formula (1). In this method, the silicon compound represented by chemical formula (1) may be used alone, or a mixture of two or more different compounds may be used.

In those cases where a mixture of two or more insulating film materials is used, there are no particular limitations on the mixing ration, which can be determined with due consideration of the dielectric constant and the copper diffusion barrier property of the obtained insulating film.

Further, during film formation, although film formation may be conducted with a carrier gas added to the insulating film material composed of the silicon compound represented by the above chemical formula (1), in terms of achieving an improved copper diffusion barrier property, the film formation is preferably conducted using only the insulating film material.

Examples of the carrier gas include gases that do not contain oxygen, and although there are no particular restrictions, specific examples of the carrier gas include rare gases such as helium, argon, krypton and xenon, as well as nitrogen, hydrogen, and hydrocarbons such as methane and ethane. A mixture of two or more gases may also be used as the carrier gas, and there are no particular restrictions on the mixing ratio between the gases, nor on the mixing ratio with the insulating film material.

Accordingly, the film formation gas that is supplied to the chamber of the film formation apparatus for the purpose of film formation may be either a gas composed solely of the insulating film material, or a mixed gas that also includes a carrier gas.

If the insulating film material and the carrier gas are gaseous at normal temperatures, they may be used as is, but if they are liquid, then a gasification must be performed prior to use. This gasification may be achieved by conducting bubbling with an inert gas such as helium, using a vaporizer, or by conducting heating.

The plasma CVD method may employ a conventional method, and for example, film formation may be conducted using a parallel plate-type plasma film formation apparatus such as that illustrated in FIG. 1.

The plasma film formation apparatus illustrated in FIG. 1 includes a chamber 1 that is able to be placed under reduced pressure, and the chamber 1 is connected to an exhaust pump 4 via an exhaust pipe 2 and an on-off valve 3. Furthermore, although not shown in the drawing, the chamber 1 is also equipped with a pressure gauge, which enables the pressure inside the chamber 1 to be measured. A pair of flat plate-shaped electrodes, namely an upper electrode 5 and a lower electrode 6, are positioned in a mutually opposing arrangement inside the chamber 1. The upper electrode 5 is connected to a high-frequency power source 7, so that a high-frequency electric current can be applied to the upper electrode 5.

The lower electrode 6 also functions as a mount for mounting a substrate 8, and a heater 9 is also provided inside the lower electrode 6, enabling the substrate 8 to be heated.

Further, a gas supply pipe 10 is connected to the upper electrode 5. A film formation gas supply source that is not shown in the drawing is connected to this gas supply pipe 10, and the film formation gas is supplied from this film formation gas supply source, passes through a plurality of through-holes formed within the upper electrode 5, and diffuses out and flows towards the lower electrode 6.

Further, the film formation gas supply source is equipped with a vaporizer for vaporizing the insulating film material and a flow rate-regulating valve for regulating the flow rate of the insulating film material, and is also provided with a supply device for supplying a carrier gas, wherein such gas also flows through the gas supply pipe 10 and enters the chamber 1 from the upper electrode 5.

The substrate 8 is mounted on top of the lower electrode 6 inside the chamber 1 of the plasma film formation apparatus, and the aforementioned film formation gas is fed from the film formation gas supply source into the chamber 1. A high-frequency current is applied to the upper electrode 5 from the high-frequency power source 7, generating a plasma inside the chamber 1. This causes the formation of an insulating film, produced by a gas-phase chemical reaction of the film formation gas, on the substrate 8.

A material composed mainly of a silicon wafer is used as the substrate 8, although other insulating films, conductive films or wiring structures or the like may be preliminarily formed on the silicon wafer.

Other plasma CVD methods that may be used besides the parallel plate-type method described above include methods that use an ICP plasma, ECR plasma, magnetron plasma, high-frequency plasma, microwave plasma, capacitively coupled plasma or inductively coupled plasma. A two-frequency excitation plasma in which a high-frequency is also supplied to the lower electrode of a parallel plate-type apparatus may also be used.

Preferred ranges for the film formation conditions within the plasma film formation apparatus are listed below, although the conditions are not necessarily restricted to these ranges.

Insulating film material flow rate: 25 to 100 cc/minute (in the case of two or more materials, this range applies to the total flow rate)

Carrier gas flow rate: 0 to 50 cc/minute

Pressure: 1 Pa to 1,330 Pa

RF power: 50 to 500 W, and preferably 50 to 250 W

Substrate temperature: not more than 400° C.

Reaction time: 1 second to 1,800 seconds

Film thickness: 100 to 200 nm

Next is a description of an insulating film of the present invention.

The insulating film of the present invention is formed using the aforementioned insulating film material for plasma CVD, or a mixture of this material and a carrier gas, by conducting a plasma CVD reaction within a plasma film formation apparatus, and has a dielectric constant within a range from 2.9 to 3.5, as well as a superior copper diffusion barrier property. Furthermore, this insulating film contains no oxygen, but is rather composed of silicon, hydrogen and carbon.

The reasons that the insulating film obtained using the insulating film formation method according to the present invention exhibits a superior copper diffusion barrier property and has a low dielectric constant are thought to be as follows.

Namely, in the cyclic structure bonded to the silicon atom of the silicon compound that constitutes the insulating film material of the present invention, the C—C portion has the lowest bond energy, and therefore this bond is cleaved by the plasma, resulting in a ring opening.

The ring-opened $CH_2$ cyclic structures accumulate on the substrate while undergoing bonding to other ring-opened $CH_2$ cyclic structures. In other words, a $CH_2$ network structure including Si—$CH_2$—$CH_2$—Si type structures is produced, and this network structure results in the formation of an insulating film which is not only dense, but also has a low dielectric constant.

Furthermore, because the insulating film material contains no oxygen, when the insulating film is formed within the plasma atmosphere, the copper that constitutes conductive films is not oxidized, meaning an insulating film is formed that is less likely to generate the copper ions that have a large effect on copper diffusion.

It is thought that for the reasons outlined above, the insulating film of the present invention has a low dielectric constant while providing a superior copper diffusion barrier property.

EXAMPLES

A more detailed description of the present invention is presented below, based on a series of examples and comparative examples. However, the scope of the present invention is in no way limited by the following examples.

Example 1

Formation of an Insulating Film without Using a Carrier Gas

A parallel plate-type capacitively coupled plasma CVD apparatus was used for forming the insulating film. An 8-inch (diameter: 200 mm) or 12-inch (diameter: 300 mm) silicon wafer was transported onto a susceptor that had been preheated to approximately 350° C., 1,1-divinyl-1-silacyclopentane was supplied to the apparatus at a volumetric flow rate of 15 cc/minute as the insulating film material gas, and an insulating film was formed with the plasma-generating high-frequency power supply set to an output of 180 W. The pressure inside the chamber of the plasma CVD apparatus during film formation was 80 Pa.

In order to measure the dielectric constant of the obtained insulating film, the silicon wafer was transported onto a CV measurement device 495 manufactured by SSM Japan, K.K., and a mercury electrode was used to measure the dielectric constant of the insulating film. The result of the measurement is listed in Table 1.

In order to evaluate the copper diffusion barrier property of the obtained insulating film, a method was employed in which the current-voltage (I-V) characteristics were compared for a copper electrode (hereafter also referred to as "the Cu electrode") and an aluminum electrode (hereafter also referred to as "the Al electrode").

This method is a Biased Temperature Stress test method which utilizes the fact that diffusion of copper into the insulating film can be accelerated by applying an electric field to the insulating film while it is heated at a temperature of approximately 100 to 300° C.

For example, if an insulating film that lacks a copper diffusion barrier property is used as the test film, then a difference develops in the I-V characteristics between the Cu electrode and the Al electrode. This difference occurs because when the electric field is applied, thermal diffusion of copper ions into the insulating film is promoted with the Cu electrode, resulting in copper ion drift that causes an increased leakage current, whereas with the Al electrode, no such thermal diffusion occurs, meaning the leakage current does not increase. Accordingly, by comparing the I-V characteristics for the Cu electrode and the Al electrode, the copper diffusion barrier property of the insulating film can be evaluated.

Figure 2:
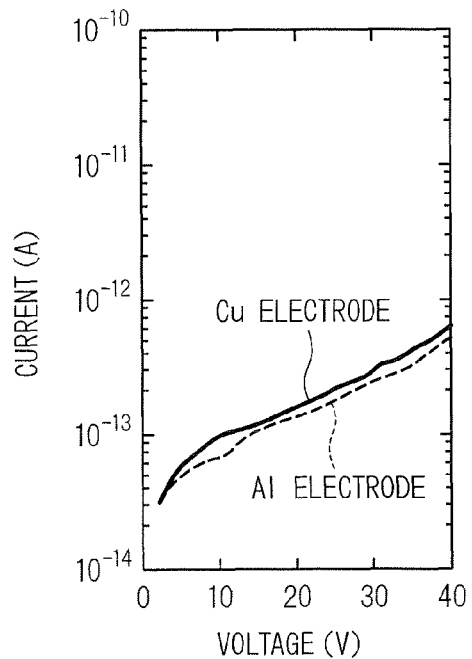
FIG. 2 is a graph illustrating a method of evaluating the copper diffusion barrier property in the present invention.

FIG. 2 is a graph illustrating the I-V characteristics for the Cu electrode and the Al electrode in the case of an insulating film having a superior copper diffusion barrier property. In other words, in this example, the I-V characteristics are substantially the same for the Cu electrode and the Al electrode.

Figure 3:
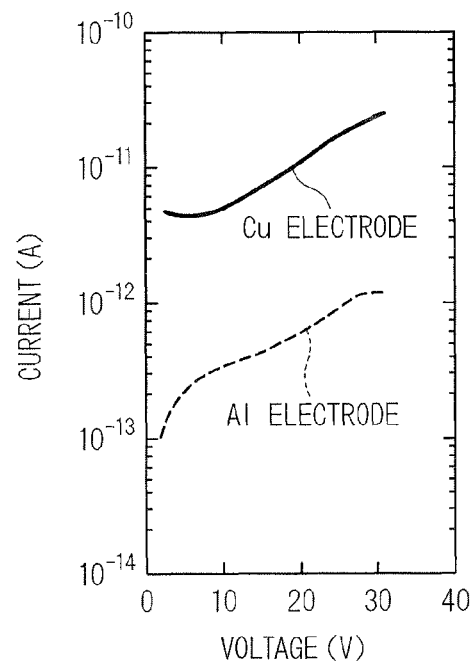
FIG. 3 is a graph illustrating a method of evaluating the copper diffusion barrier property in the present invention.

FIG. 3 is a graph illustrating the I-V characteristics in the case of an insulating film with a poor copper diffusion barrier property. In this example, there is a significant difference between the I-V characteristics for the Cu electrode and the I-V characteristics for the Al electrode, with the current value of the I-V characteristics observed with the Cu electrode being two orders of magnitude or more greater than the current value of the I-V characteristics observed with the Al electrode.

In this manner, those films for which the current values are substantially equal for the I-V characteristics observed with the Cu electrode and the I-V characteristics observed with the Al electrode are considered to have a superior copper diffusion barrier property, whereas those films for which a difference of one order of magnitude or greater occurs between the current value of the I-V characteristics observed with the Cu electrode and the current value of the I-V characteristics observed with the Al electrode are considered to have a poor copper diffusion barrier property.

Details relating to this test method are available by reference to the publication listed below.

Alvin L. S. Loke et al., IEEE TRANSACTIONS ON ELECTRON DEVICES, VOL. 46, NO. 11, 2178-2187 (1999).

A specific description of the procedure used for evaluating the copper diffusion barrier property of an insulating film is described below.

Firstly, two measurement samples cut to a size of approximately 30 mm$^2$ were prepared, masks were applied to the samples, and a vacuum deposition method was used to form a Cu electrode having a diameter of approximately 1 mm on one sample, and an Al electrode having a diameter of approximately 1 mm on the other sample.

Subsequently, the measurement sample on which the Cu electrode had been formed was mounted within a vacuum probe apparatus, the inside of the apparatus was evacuated down to a vacuum atmosphere of not more than 0.133 Pa, and the I-V characteristics were measured using the CV measurement device mentioned above. Nitrogen was then supplied to the vacuum probe apparatus to raise the pressure to approximately 93 kPa, the stage temperature was heated to a temperature of 140° C. or 200° C., and the I-V characteristics were measured using the above CV measurement device.

Figure 4:
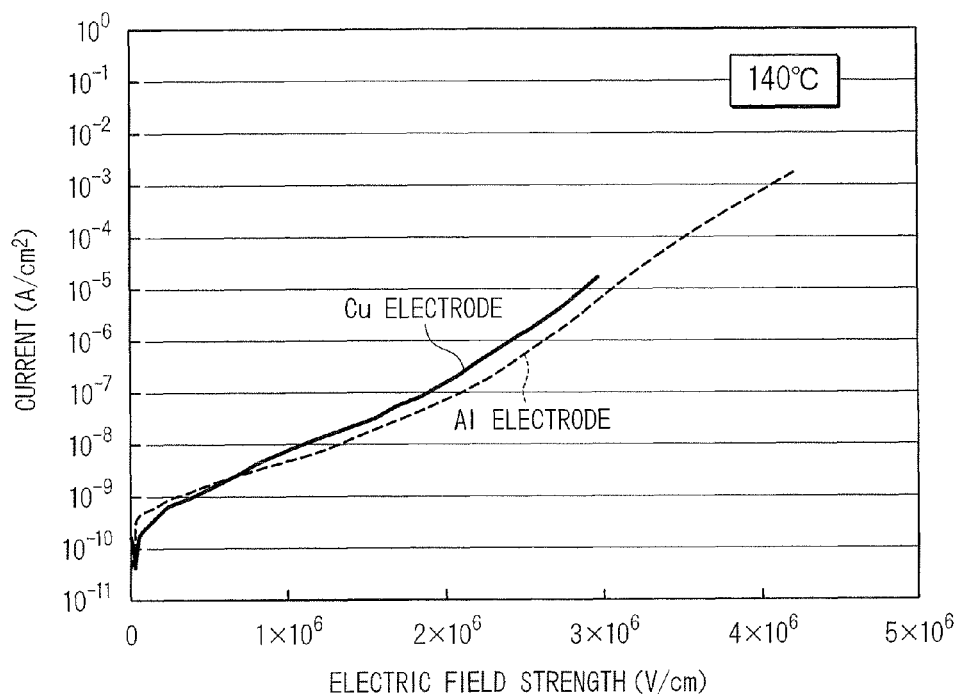
FIG. 4 is a graph illustrating the results of evaluating the copper diffusion barrier property in an example 1.

This procedure for measuring the I-V characteristics for the measurement sample on which the Cu electrode had been formed was repeated for the measurement sample on which the Al electrode had been formed, and the copper diffusion barrier property of the insulating film formed was then evaluated based on the difference between the I-V characteristics with the Cu electrode and the Al electrode. The results are illustrated in FIG. 4.

Measurement of the film thickness of the insulating film was conducted using a spectroscopic ellipsometer manufactured by FiveLab Co., Ltd. The result of the measurement is shown in Table 1.

Example 2

Formation of an Insulating Film Using a Carrier Gas

The apparatus and method used for forming the insulating film were substantially the same as those employed in example 1, although as the material gas, 1,1-divinyl-1-silacyclopentane was supplied at a volumetric flow rate of 17 cc/minute, and helium was supplied simultaneously as a carrier gas at a flow rate of 40 cc/minute. The insulating film was formed with the plasma-generating high-frequency power supply set to an output of 150 W. The pressure inside the chamber of the plasma CVD apparatus during film formation was 133 Pa.

Figure 5:
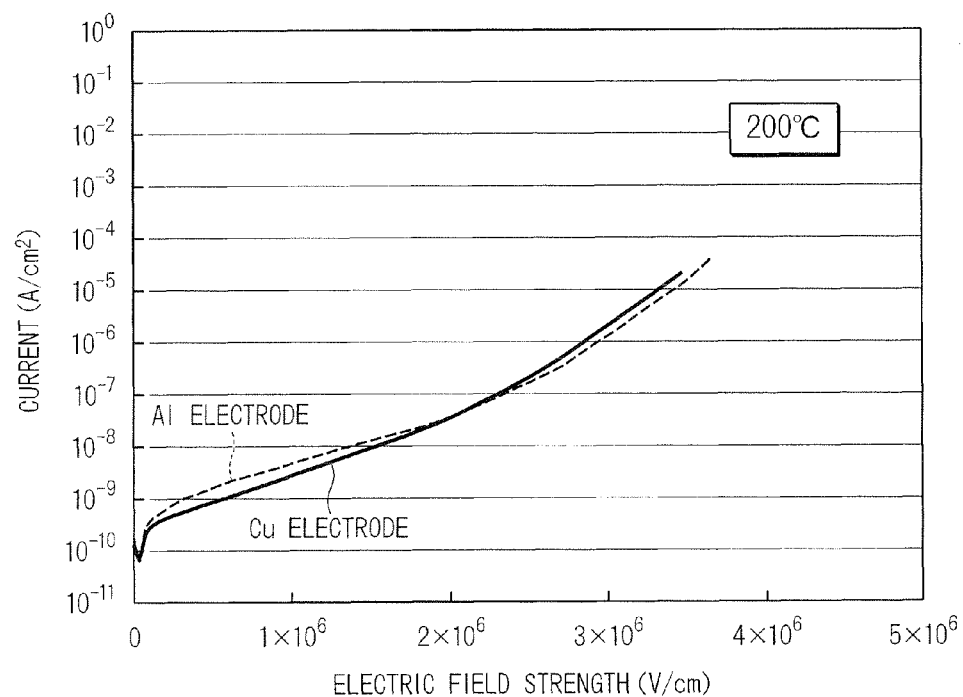
FIG. 5 is a graph illustrating the results of evaluating the copper diffusion barrier property in an example 2.

The dielectric constant, the copper diffusion barrier property and the film thickness of the obtained insulating film were evaluated in the same manner as example 1. The measurement results are shown in Table 1. The results of evaluating the copper diffusion barrier property are illustrated in FIG. 5.

Comparative Example 1

Formation of an Insulating Film Using a Material Gas Containing No Cyclic Structure Composed of $CH_2$ Groups The apparatus and method used for forming the insulating film were substantially the same as those employed in example 1, although as the material gas, tetravinylsilane was supplied at a volumetric flow rate of 30 cc/minute, and helium was supplied simultaneously as a carrier gas at a flow rate of 30 cc/minute. The insulating film was formed with the plasma-generating high-frequency power supply set to an output of 100 W. The pressure inside the chamber of the plasma CVD apparatus during film formation was 798 Pa.

Figure 6:
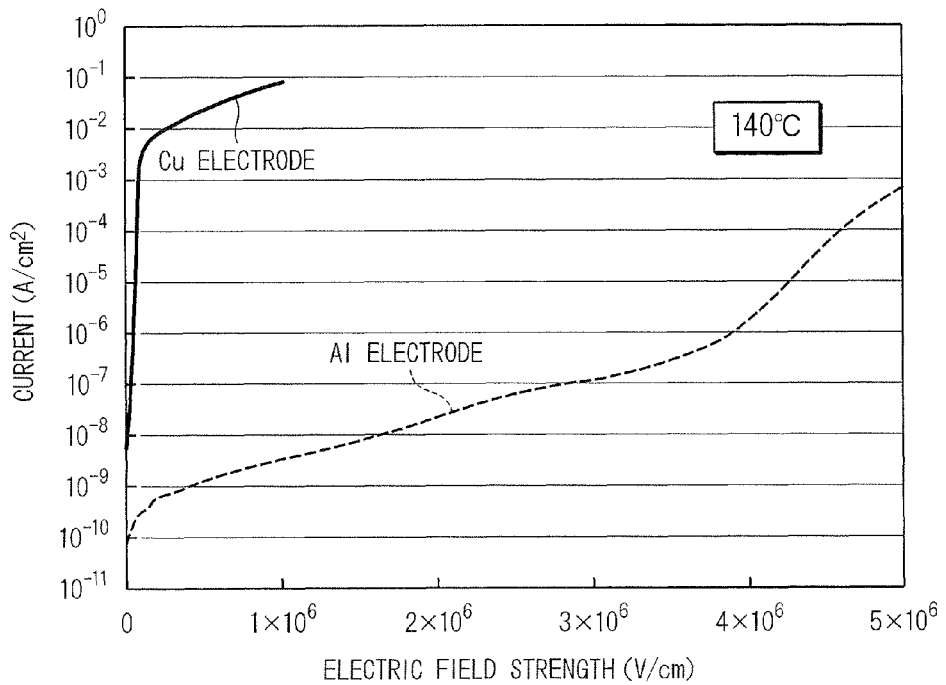
FIG. 6 is a graph illustrating the results of evaluating the copper diffusion barrier property in a comparative example 1.

The dielectric constant, the copper diffusion barrier property and the film thickness of the obtained insulating film were evaluated in the same manner as example 1. The measurement results are shown in Table 1. The results of evaluating the copper diffusion barrier property are illustrated in FIG. 6.

Comparative Example 2

Formation of an Insulating Film Using a Material Gas Containing No Cyclic Structure Composed of $CH_2$ Groups The apparatus and method used for forming the insulating film were substantially the same as those employed in example 1, although as the material gas, diallyldivinylsilane was supplied at a volumetric flow rate of 30 cc/minute, and helium was supplied simultaneously as a carrier gas at a flow rate of 30 cc/minute. The insulating film was formed with the plasma-generating high-frequency power supply set to an output of 100 W. The pressure inside the chamber of the plasma CVD apparatus during film formation was 133 Pa.

Figure 7:
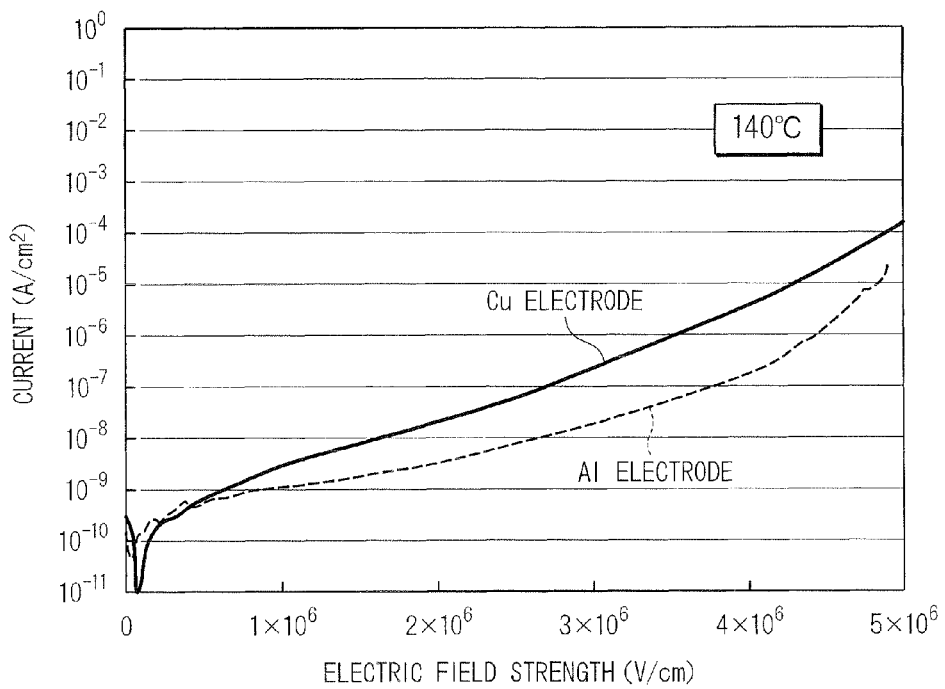
FIG. 7 is a graph illustrating the results of evaluating the copper diffusion barrier property in a comparative example 2.

The dielectric constant, the copper diffusion barrier property and the film thickness of the obtained insulating film were evaluated in the same manner as example 1. The measurement results are shown in Table 1. The results of evaluating the copper diffusion barrier property are illustrated in FIG. 7.

TABLE 1

|  | Dielectric constant | Copper diffusion barrier property | Film thickness |
| --- | --- | --- | --- |
| Example 1 | 3.08 | Yes | 189 nm |
| Example 2 | 3.38 | Yes | 193 nm |

TABLE 1-continued

|  | Dielectric constant | Copper diffusion barrier property | Film thickness |
| --- | --- | --- | --- |
| Comparative example 1 | 2.87 | No | 205 nm |
| Comparative example 2 | 2.72 | No | 269 nm |

As is evident from the results listed in Table 1 and the graphs of FIG. 4 to FIG. 7, the insulating film formed in example 1 had a dielectric constant of 3.08 and exhibited a copper diffusion barrier property, and the insulating film formed in example 2 had a dielectric constant of 3.38 and exhibited a copper diffusion barrier property. In contrast, the insulating film formed in comparative example 1 had a dielectric constant of 2.87 but lacked a copper diffusion barrier property, and the insulating film formed in comparative example 2 had a dielectric constant of 2.72 but lacked a copper diffusion barrier property.

As described above, by forming an insulating film by a plasma CVD method using a silicon compound represented by the above chemical formula (1) as the insulating film material, an insulating film can be formed that exhibits a superior copper diffusion barrier property and has a low dielectric constant. Further, by performing the film formation without using a carrier gas such as helium, an insulating film with a superior copper diffusion barrier property that has an even lower dielectric constant suitable for next generation applications can be formed.

Industrial Applicability

The present invention can be applied to semiconductor devices that use the type of highly integrated LSI wiring required in next generation applications.

The invention claimed is:

1. A method of film formation, comprising using an insulating film material to form an insulating film by a plasma CVD method, wherein
the insulating film material is a compound represented by chemical formula (1) shown below;

[Chemical Formula 1]

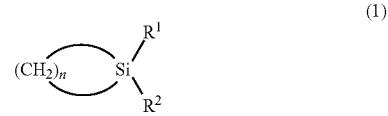

(1)

wherein n represents an integer of 3 to 6, $R^1$ represents one of $C_2H$, $C_2H_3$, $C_3H_3$, $C_3H_5$, $C_4H_5$, $C_4H_7$, $C_5H_7$, and $C_5H_9$, and $R^2$ represents one of $C_2H$, $C_2H_3$, $C_3H_3$, $C_3H_5$, $C_3H_7$, $C_4H_5$, $C_4H_7$, $C_4H_9$, $C_5H_7$, $C_5H_9$, and $C_5H_{11}$.

2. The method of film formation according to claim 1, wherein a carrier gas is not supplied during film formation.

3. An insulating film, obtained by the method of film formation according to claim 1.

4. An insulating film, obtained by the method of film formation according to claim 2.

* * * * *